(12) United States Patent
Wang

(10) Patent No.: US 7,322,051 B1
(45) Date of Patent: Jan. 29, 2008

(54) FASTENING STRUCTURE FOR HEADBAND OF SKI GOGGLES

(75) Inventor: Ching-Hsiang Wang, Tainan (TW)

(73) Assignee: Day Sun Industrial Corp., Tainan (TW)

( * ) Notice: Subject to any disclaimer, the term of this patent is extended or adjusted under 35 U.S.C. 154(b) by 0 days.

(21) Appl. No.: 11/683,700

(22) Filed: Mar. 8, 2007

(51) Int. Cl.
*A61F 9/02* (2006.01)
(52) U.S. Cl. ........................................... 2/448
(58) Field of Classification Search .................... 2/428, 2/430, 448, 452; 24/199
See application file for complete search history.

(56) References Cited

U.S. PATENT DOCUMENTS 7,003,811 B2 * 2/2006 Canavan .................. 2/448
7,162,750 B2 * 1/2007 Canavan .................. 2/448

* cited by examiner

*Primary Examiner*—Katherine Moran
(74) *Attorney, Agent, or Firm*—Alan Kamrath; Kamrath & Associates PA

(57) ABSTRACT

A headband fastening structure for ski goggles includes a lens fitted in a goggle frame and a headband. The lens and having a pair of extending segments on opposite sides, each extending segments is provided with a wedge portion upwardly sloped toward the front thereof and a recess on one side adjacent the goggle frame. A fixing hole is provided on each of the fastening segments, wherein each of the inset segments extending along the inner side of each of the fastening segments with a predetermined interval. The insert segments are inserted into the respective recesses of the extending segments of the lens. Each fixing holes is pushed toward the corresponding wedge portion smoothly and gradually along the slope of the wedge portion until the fixing hole retains the wedge portion firmly. The ski goggles and the headband are thus assembled together and positioned in a prompt and steady manner.

1 Claim, 4 Drawing Sheets

FASTENING STRUCTURE FOR HEADBAND OF SKI GOGGLES

BACKGROUND OF THE INVENTION

1. Technical Field

The present invention relates to a fastening structure for a headband of ski goggles and, more particularly, to a novel design whereby the goggle frame and the headband of ski goggles for sports use can be easily and promptly fastened together and positioned steadily.

2. Description of Related Art

Currently, regarding ski goggles for sports use, there are various means for fastening a goggle frame and a headband for fitting onto a user's head. For example, there may be a pair of openings provided at opposite sides of a frame of ski goggles respectively for allowing a headband to be pierced therethrough manually, and then both ends of the headband can be positioned fixedly by sewing. Though such a conventional headband assembled to opposite sides of the ski goggles can provide comfortable touch for users, the manual operation required for fastening the headband to the goggle frame by piercing the headband through the openings and sewing connecting segments of the headband subsequently is indispensable. Thus, the manufacturing process of such conventional ski goggles is relatively inconvenient. Also, once the headband is worn out, the headband cannot be promptly detached and replaced.

SUMMARY OF THE INVENTION

The present invention has been accomplished under these circumstances in view. It is one objective of the present invention to provide an improved fastening structure for a ski goggle frame and a headband to be fastened to opposite sides thereof, which facilitates prompt assembly of the ski goggle frame and the headband during manufacture, and in turn significantly enhances the processing efficiency while reducing the costs of fabrication.

To achieve these and other objectives of the present invention, the disclosed fastening structure for ski goggles comprises a lens fitted in a goggle frame and a headband. The lens has a pair of extending segments extending backward from opposite sides. Each of the extending segments is provided with a wedge portion upwardly sloped toward the front thereof and a recess on one side adjacent the goggle frame, sized for snugly receiving an inset segment of the headband. A fixing hole is provided on each of the fastening segments and shaped for snugly accommodating the corresponding wedge portion. Each of the inset segments extends along the inner side of each of the fastening segments with a predetermined interval. Whereby each of the insert segments is inserted into each of the recesses of the extending segments of the lens, and each of the fixing holes is pushed toward the corresponding wedge portion smoothly and gradually along the slope of the wedge portion until the fixing hole retains the wedge portion firmly. The ski goggles and the headband are thus assembled together and positioned in a prompt and steady manner.

BRIEF DESCRIPTION OF THE DRAWINGS

The invention as well as a preferred mode of use, further objectives and advantages thereof, will be best understood by reference to the following detailed description of an illustrative embodiment when read in conjunction with the accompanying drawings, wherein.

DETAILED DESCRIPTION OF THE PREFERRED EMBODIMENT

Figure 1:
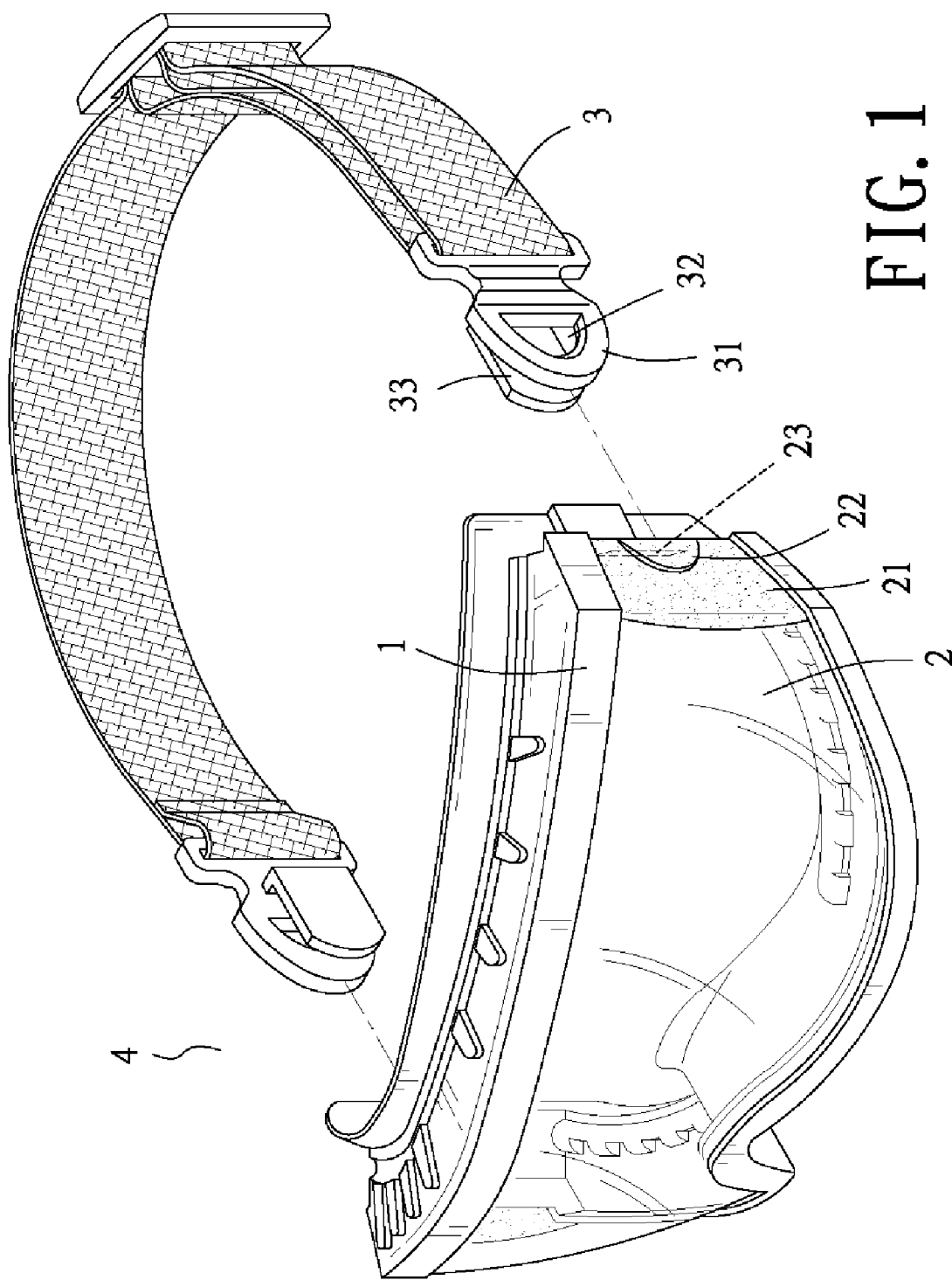
FIG. 1 is an exploded view of ski goggles and a headband of the present invention.

Referring to FIG. 1, a fastening structure for headband of ski goggles is shown. The ski goggles 4 comprise a goggle frame 1, a lens 2 fitting the shape of and combined with the goggle frame 1, and a headband 3 having proper elasticity.

The lens 2 combined with the goggle frame 1 is shaped to fit the shape of the goggle frame 1 and provided with two extending segments 21 extending backward from opposite sides of the lens 2 respectively. On each of the extending segments 21, a wedge portion 22 is formed near the outer edge thereof and upwardly sloped toward the front thereof. Further, a recess 23 is provided on one end of each of the extending segments 21 of the lens 2 near the goggle frame 1, and is sized for snugly receiving each of insert segments 33 at opposite ends of the headband 3.

The headband 3 is provided with a pair of fastening segments 31 at the opposite ends respectively. A fixing hole 32 shaped for snugly accommodating each of the wedge portions 22 formed on the lens 2 is provided on each of the fastening segments 31. Additionally, each of the insert segments 33 extends along the inner side of each of the fastening segment 31 with a predetermined interval.

Figure 2:
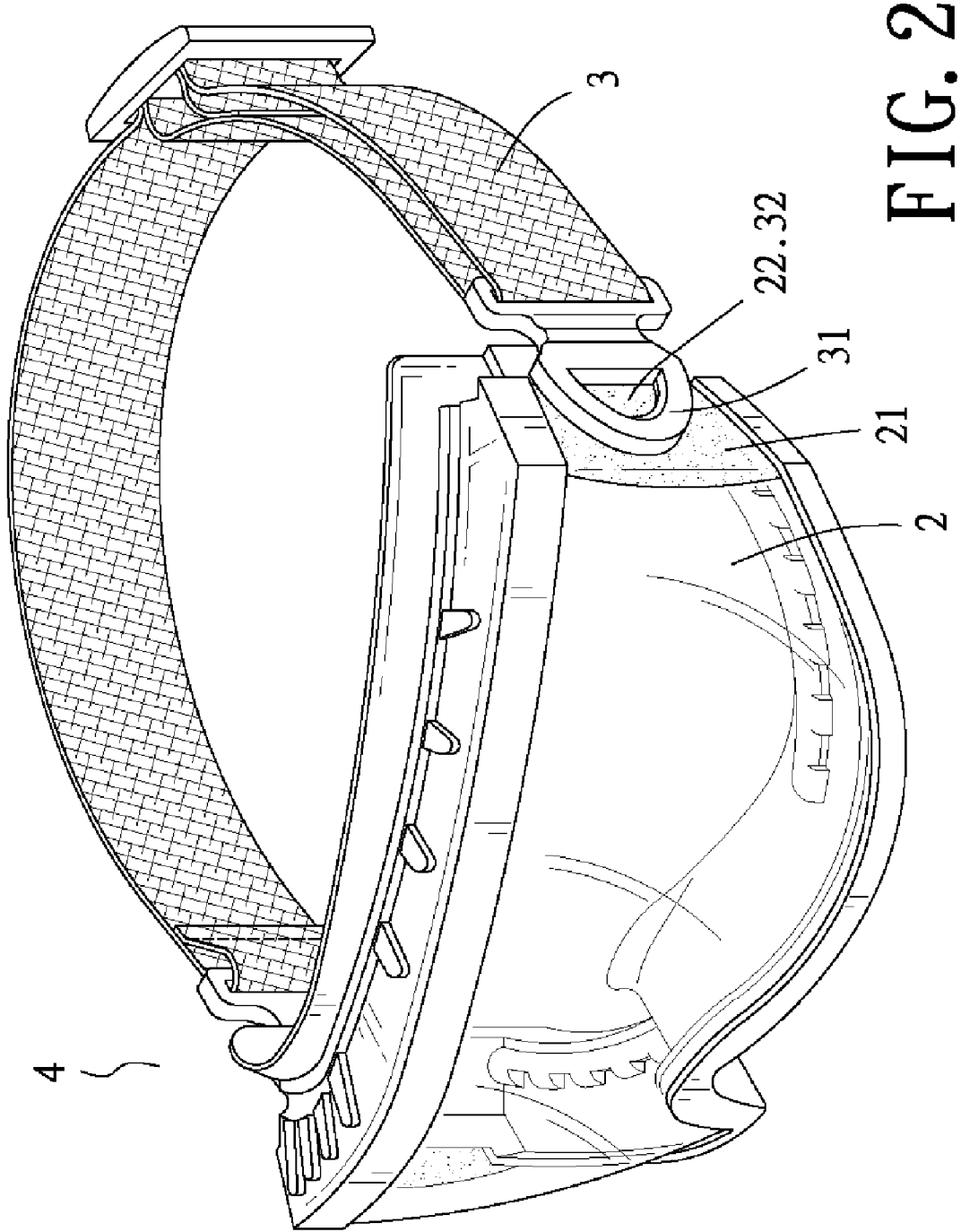
FIG. 2 is an assembly drawing of the ski goggles and the headband of the present invention.
Figure 3:
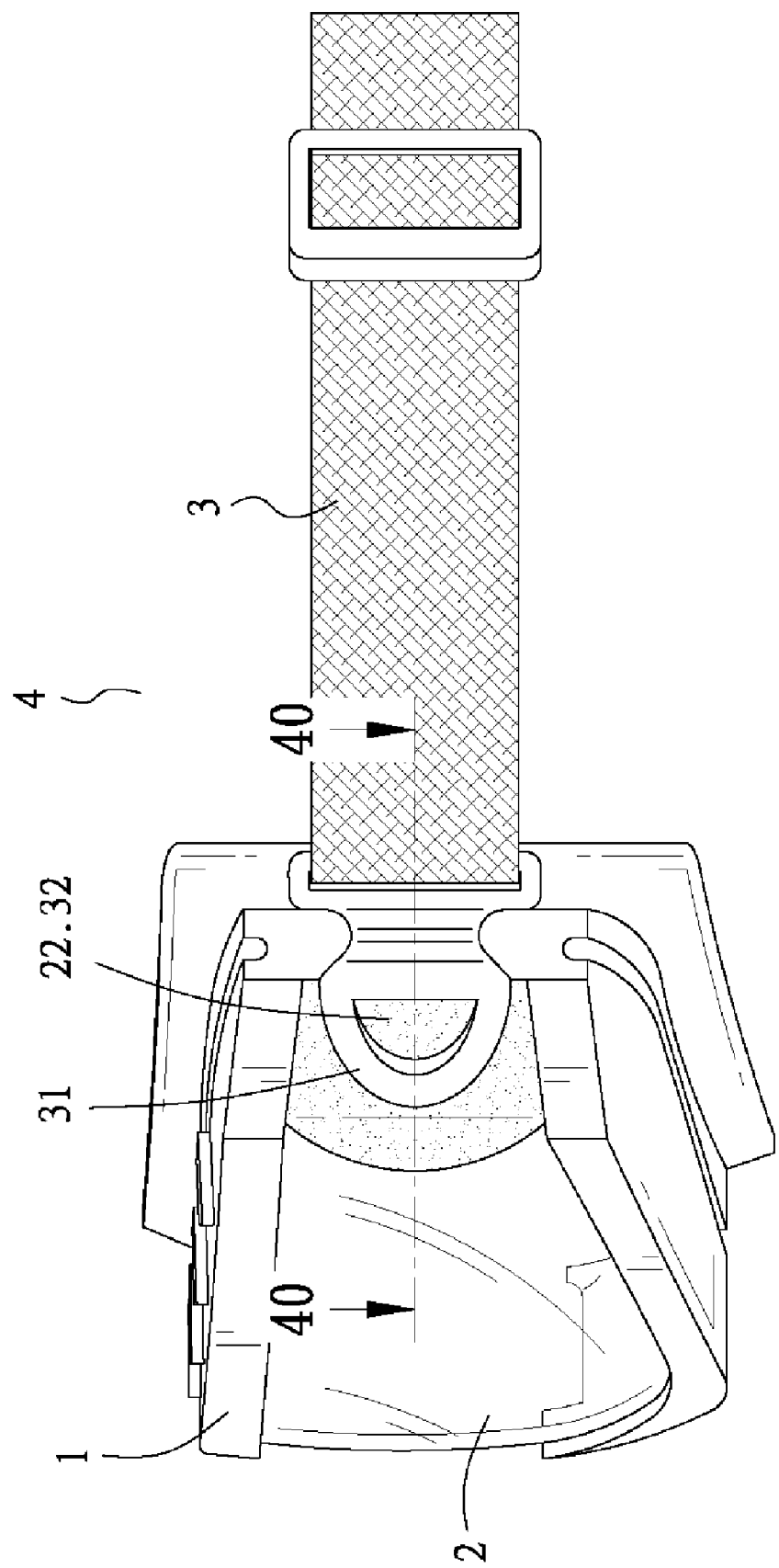
FIG. 3 is a lateral view of the assembled ski goggles and headband of the present invention.
Figure 4:
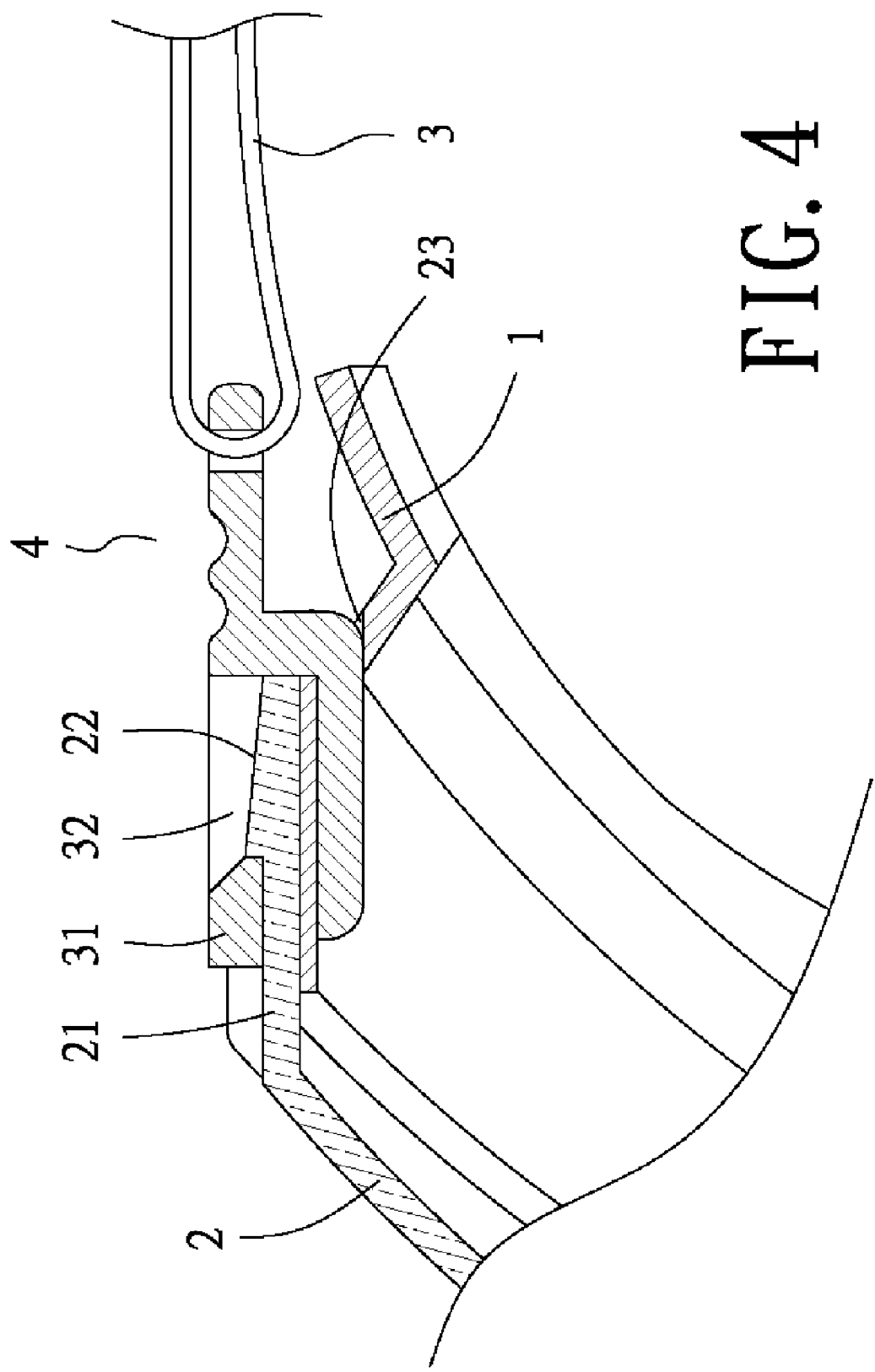
FIG. 4 is a sectional view taken in an enlarged scale along line 40-40 of FIG. 3.

To assemble the lens 2 combined with the frame 1 and the headband 3, referring to FIGS. 1 and 4, the insert segments 33 provided respectively at the opposite ends of the headband 3 are inserted into the recesses 23 of the extending segments 21 of the lens 2 fitted in the frame 1. Thereby, the insert segments 33 can be against side surfaces of the frame 1 respectively. Then each of the fixing holes 32 of the headband 3 is pushed toward the corresponding wedge portion 22 smoothly and gradually along the slope of the wedge portion 22 until the fixing hole 32 retains the wedge portion 22 firmly, as shown in FIGS. 2 and 3. Thereupon, the ski goggles 4 and the headband 3 can be assembled together and positioned in a prompt and steady manner.

Foresaid fastening structure between the lens fitted in the frame and the headband provides following advantages:

1. Formation of the wedge portions formed on the extending segments of the lens mounted on the ski goggle frame, and the fastening segments as well as the insert segments formed at the opposite ends of the headband can be accomplished by means of mold making technology. Hence, the manufacturing process and the assembling of the lens and the headband can be made easier and prompter.

2. After being assembled, the lens of the ski goggles mounted on the frame and the headband are combined and positioned steadily. If a user later intends to disassemble the headband for installing another headband of different type, he needs only to pull the fastening segments outward to make the fixing holes release the corresponding wedge portions, so that the lens and the headband can be disassembled, and the user can substitute another band for the original one and reassemble it to the lens instead.

Although a particular embodiment of the invention has been described in details for purposes of illustration, it will be understood by one of ordinary skill in the art that numerous variations will be possible to the disclosed embodiment without going outside the scope of the invention as disclosed in the claims.

What is claimed is:

1. A fastening structure for a headband of ski goggles comprising:
- a lens fitted in a goggle frame and having a pair of extending segments respectively extending backward from opposite sides of the lens, each of the extending segments being provided with a wedge portion upwardly sloped toward the front thereof and a recess on one side adjacent the goggle frame, sized for snugly receiving an inset segment of the headband; and
- a fixing hole provided on each of the fastening segments and shaped for snugly accommodating the corresponding wedge portion, wherein each of the inset segments extending along the inner side of each of the fastening segments with a predetermined interval;

whereby each of the insert segments is inserted into each of the recesses of the extending segments of the lens, and each of the fixing holes is pushed toward the corresponding wedge portion smoothly and gradually along the slope of the wedge portion until the fixing hole retains the wedge portion firmly, so that the ski goggles and the headband are assembled together and positioned in a prompt and steady manner.

* * * * *